United States Patent
Teder

(10) Patent No.: US 6,268,612 B1
(45) Date of Patent: Jul. 31, 2001

(54) MOISTURE SENSOR WITH AUTOBALANCE CONTROL

(75) Inventor: Rein S. Teder, Bloomington, MN (US)

(73) Assignee: Libbey-Owens-Ford Co., Toledo, OH (US)

(*) Notice: Subject to any disclaimer, the term of this patent is extended or adjusted under 35 U.S.C. 154(b) by 0 days.

(21) Appl. No.: 09/592,515

(22) Filed: Jun. 12, 2000

Related U.S. Application Data

(63) Continuation of application No. 09/223,584, filed on Dec. 30, 1998, now Pat. No. 6,078,056.

(51) Int. Cl.$^7$ .................................................. G02B 6/42
(52) U.S. Cl. ...................... 250/574; 318/483; 250/214 A
(58) Field of Search .................................. 250/574, 216, 250/214 R, 214 A, 214 C; 318/443, 444, 483, 484, DIG. 2; 340/602

(56) References Cited

U.S. PATENT DOCUMENTS 4,355,271 * 10/1982 Noack .................................. 318/483

6,078,056 * 6/2000 Teder ................................... 250/574

* cited by examiner

*Primary Examiner*—John R. Lee
*Assistant Examiner*—Kevin Pyo
(74) *Attorney, Agent, or Firm*—Marshall & Melhorn, LLC.

(57) ABSTRACT

An autobalance control circuit for use in a moisture sensor which senses moisture on the surface of a transparent material. The moisture sensor includes detectors for receiving emitter signals which are influenced by moisture on the transparent material. The moisture sensor further includes a pre-demodulation circuit for attenuating unwanted signal components in the detector output signal while amplifying the useful signal components for further processing by a microprocessor. An autobalance circuit is provided for receiving the pre-demodulation circuit signal and providing an autobalance signal to the pre-demodulation circuit input. The autobalance signal at least partially cancels the detector output signal to prevent saturation of the pre-demodulation amplifier when undesirable detector output signal amplitudes are encountered. By preventing saturation of the moisture sensor circuitry, the autobalance circuit allows the sensor to continue to operate in the presence of large drops of moisture while having sufficient gain for detecting small droplets of moisture.

20 Claims, 4 Drawing Sheets

MOISTURE SENSOR WITH AUTOBALANCE CONTROL

CROSS REFERENCE TO RELATED APPLICATIONS

This application is continuation of the utility application, Ser. No. 09/223,584, filed Dec. 30, 1998 now U.S. Pat. No. 6,078,056. The utility application Ser. No. 09/223,584 is hereby incorporated by reference.

BACKGROUND OF THE INVENTION

The present invention relates generally to an optical moisture sensor for detecting moisture on the surface of a transparent material, and more particularly, to a moisture sensor autobalance circuit for preventing saturation of the sensor amplifiers.

The accumulation of moisture on transparent materials, such as glass or Plexiglass, can obstruct a person's view through the material. Motor vehicles have long been equipped with motor-driven windshield wipers for clearing the moisture from the external surface of the windshield, at least within the driver's field of vision, and generally over a larger area so as to enhance one's vision through the windshield.

In most vehicles today, the windshield wiper system includes multi-position or variable speed switches which allow the driver to select a wide, if not an infinitely variable, range of speeds to suit conditions. Wiper controls are manually operated and typically include a delay feature whereby the wipers operate intermittently at selected time delay intervals.

Wiper control systems have recently been developed which include a moisture sensor mounted on one of the vehicle windows to automatically activate the wiper motor when moisture is deposited upon the surface of the window. The wiper control system including the moisture sensor are most typically mounted on the windshield, although the system may be mounted on the rear window or any other glass surface intended to be cleared of moisture. Such wiper control systems free the driver from the inconvenience of frequently adjusting the wiper speed as the driving conditions change.

Wiper control systems have used a number of different technologies to sense the moisture conditions encountered by a vehicle, including conductive, capacitive, piezoelectric, and optical sensors. Optical sensors operate upon the principle that a light beam is diffused or deflected from its normal path by the presence of moisture on the exterior surface of the windshield. The systems which employ optical sensors have the singular advantage that the means of sensing disturbances in an optical path is directly related to the phenomena observed by the driver (i.e., disturbances in the optical path that affords the driver vision). McCumber et al. (U.S. Pat. No. 4,620,141) disclose an optical moisture sensor which triggers a sweep of the wiper blades in response to the presence of water droplets on the exterior surface of a windshield.

In optical moisture sensors, a light signal from an emitter is directed into the windshield and reflected back by the outer surface of the windshield and into a detector. The presence of moisture on the surface of the windshield affects the reflection of the light signal at the outer surface of the windshield resulting in a reflected signal having a lower amplitude. The detector receives the reflected signal and produces an output signal which indicates the change in amplitude of the reflected emitter signal. The detector output signal also contains noise and other unwanted signals such as those from ambient light and electromagnetic interference. These undesirable signal components must be removed from the detector output signals before accurate moisture readings can be obtained.

It is known to use high pass and low pass filters to remove unwanted signal components from the detector signals. Noack, in U.S. Pat. No. 4,355,271, shows a moisturesensor with a detector having an output connected to a filter. The filter rejects the low frequency components of the signal from the detector, and provides gain to the signal. The signal is subsequently demodulated using a rectifier, and compared against a threshold. The filter of '271 is thus a pre-demodulation filter which acts on the signal before a demodulator converts the pulsatile signal into a dc signal that is affected by sensed moisture.

However, the use of pre-demodulation gain tends to make the gain stage circuitry prone to saturation, in which the output of the amplifier reaches the upper or lower limits of the sensor power supply. For example, large moisture drops tend to cause large changes in the signal emanating from the detectors. If a signal arising from a large drop should cause the gain stage output to reach either of those limits, the output can go no further and saturates. When operating under these conditions, the moisture sensor system becomes insensitive to further changes in the detector output and loses the ability to accurately detect moisture. It is desirable to prevent saturation to keep the sensor operating under similar conditions.

The tendency of the gain stage circuitry to saturate limits how much gain the circuitry may provide. This, in turn, limits the ability of the moisture sensor to detect small droplets of moisture. Small droplets of moisture lead to very small changes in the signal from the detectors. If the gain of the pre-demodulation circuitry is kept low enough so that large drops do not cause the pre-demodulation circuitry to saturate, then the signal arising from small drops will be too small to be detected by subsequent processing. Thus it is desirable to prevent saturation, so that the gain of the system may be sufficient to detect small drops.

SUMMARY OF THE INVENTION

An autobalance control circuit for use in a moisture sensor which senses moisture on the surface of a transparent material. The moisture sensor includes one or more emitters for producing emitter signals which are influenced by moisture on the transparent material, and one or more detectors for receiving the emitter signals. The detector produces a detector output signal which is processed by moisture sensing circuitry, including a microprocessor, for determining the presence of moisture. The moisture sensor further includes a pre-demodulation circuit for attenuating unwanted signal components in the detector output signal while amplifying the useful signal components for further processing.

An autobalance circuit is provided for receiving the pre-demodulation circuit signal and providing an autobalance signal to the pre-demodulation circuit input. The autobalance signal at least partially cancels the detector output signal to prevent saturation of the pre-demodulation amplifier when undesirable detector output signal amplitudes are encountered. The autobalance circuit includes an averaging circuit for averaging the pre-demodulation signal which is used to at least partially cancel the detector output signal. By preventing saturation of the circuitry of the moisture sensor, the autobalance circuit allows the sensor to continue to operate in the presence of large drops of moisture, and to have sufficient gain for detecting small droplets of moisture.

BRIEF DESCRIPTION OF THE DRAWINGS

The advantages of the invention will become readily apparent to those skilled in the art from the following detailed description of a preferred embodiment when considered in the light of the accompanying drawings, in which.

DETAILED DESCRIPTION OF THE PREFERRED EMBODIMENTS

It is to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
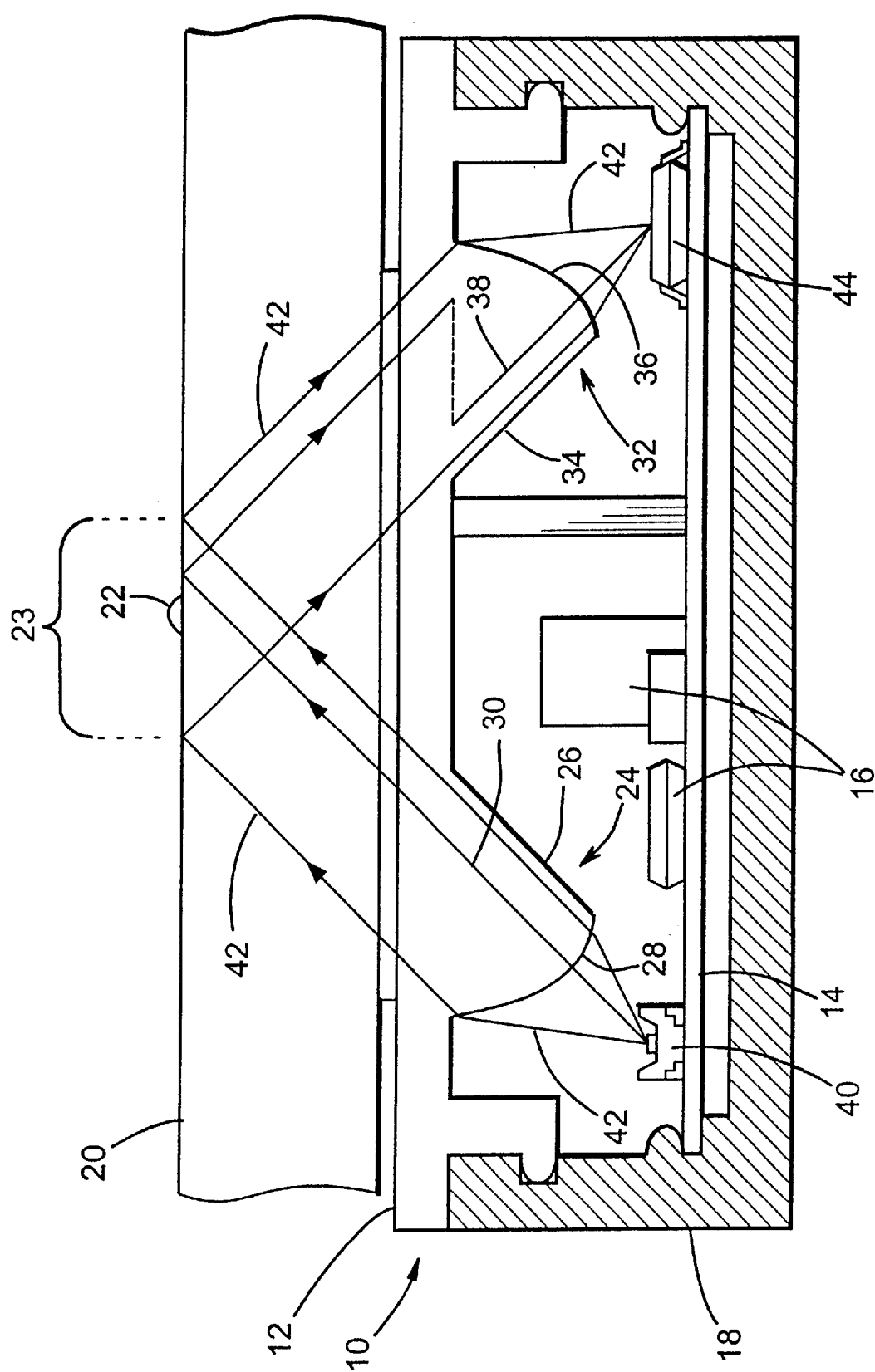
FIG. 1 is a perspective view of a moisture sensor mounted on the inner surface of the windshield in accordance with the invention.

Referring now to FIG. 1, an optoelectronic moisture sensor is shown generally at 10. The moisture sensor includes a coupler 12, a circuit board 14 for mounting electronic components 16, and a sensor housing 18 attachable to the coupler 12 for enclosing the circuit board 14.

The coupler 12 is secured to a first surface of a transparent material 20 for the optical detection of moisture 22 on the oppositely disposed, second surface of the transparent material. The transparent material 20 is preferably glass, such as an automotive windshield or freezer door, although the moisture sensor may be used to detect moisture on Plexiglas, plastic or any other transparent material.

The coupler 12 includes a collimator 24 including a collimating body 26 extending from the coupler and a collimating lens 28 disposed adjacent to the collimating body. The collimating lens 28 has an optical axis 30 which extends through the collimating body 26 at a forty-five degree angle with respect to the inner surface of the glass 20. The coupler 12 further includes a focuser 32 having a focusing body 34 extending from the coupler and a focusing lens 36 disposed adjacent to the focusing body. The focusing lens 36 has an optical axis 38 which extends through the focusing body 34 at a forty-five degree angle with respect to the inner surface of the glass 20.

An optoelectonic signal emitter 40 is disposed on the circuit board 14 adjacent the collimator 24 for emitting a signal indicated at 42. The signal emitter 40 is preferably an infrared light-emitting diode, although any suitable signal emitter may be used. The emitted signal 42 is preferably an infrared radiation signal, that is infrared light, although any suitable signal may be used. A detector 44 is disposed on the circuit board 40 adjacent the focuser 32. The detector 44 is preferably a photodiode, although any suitable detector for receiving the emitter signal 42 may be used.

During operation of the moisture sensor, the emitter 40 emits an infrared signal 42 which travels to the focusing lens 28 of the collimator 26. The emitted signal 42 is collimated into a collimated beam which travels along the optical axis 30 and into the glass 20 at a forty-five degree angle with respect to the inner surface of the glass. The collimated signal 42 strikes the outer surface of the glass 20 at a sensing region 23 where the presence of moisture can be detected. The collimated signal 42, or at least a portion of the signal is then reflected back through the glass 20 and into the focusing body 34 at a forty-five degree angle with respect to the glass. The focusing lens 28 focuses the reflected signal 42 onto the detector 44.

If moisture 22 has accumulated on the windshield in the sensing region 23, a portion of the collimated light beam 42 will not be reflected back to the focusing body 34 and the detector 44 will produce a signal representative of the lesser amount of light which is detected. The moisture sensing circuitry 16 receives the detector signal and interprets the change in the signal as the presence of moisture and controls the wipers accordingly.

Additional details concerning the operation of the optical portion of the moisture sensor and the interface with the wiper control system may be obtained from U.S. Pat. Nos. 4,620,141; 5,059,877; 5,239,244; and 5,568,027, and U.S. application No. 08/951,922 filed Oct. 16, 1997. To the extent any such details may be necessary to complete the descriptions and accounts necessary for purposes of the present application, these references are deemed to be incorporated by reference herein. While the moisture sensor described above is an optoelectronic moisture sensor, any suitable moisture sensor may be used in which the emitted signal received by a detector is used for detecting the presence of moisture on the surface of a transparent material.

Figure 2:
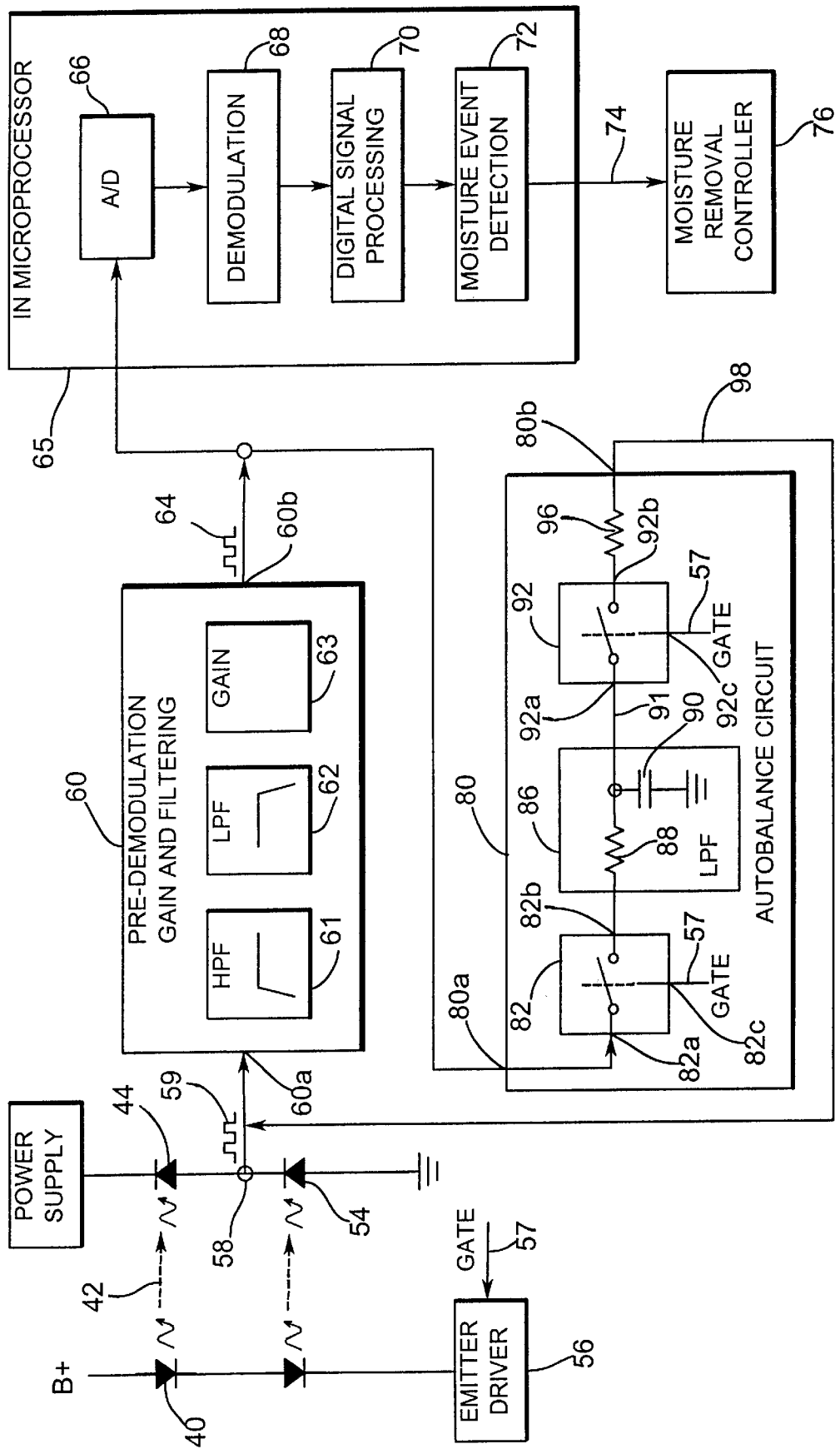
FIG. 2 is a block diagram of the moisture sensor illustrated in FIG. 1 including the autobalance circuit in accordance with the invention.

Referring now to FIG. 2, a block diagram of the moisture sensor 10 is illustrated. The preferred embodiment of the moisture sensor includes a pair of emitters 40 communicating with a pair of detectors 44 for detecting moisture as described above. An emitter driver 56 is connected to the emitters 40 for providing power to the emitters in an amount which determines the amplitude or intensity of the emitter signals 42. A periodically repeating gate signal pulse 57 is applied to emitter driver 56 as described below.

The detectors 44 are coupled with the emitters 40 for receiving at least a portion of the emitter signals 42 and respond by producing detector signals (not shown). In the preferred embodiment, each detector 44 is preferably optically coupled for receiving the emitter signal 42 from each emitter 40, in a similar manner as described above, to create four sensing regions 23 on the transparent material. However, any suitable number of emitters 40 and detectors 44 may be used to create any desired number sensing regions 23.

The detectors 44 are connected to a common node 58 where the detector signals are combined to produce a detector output signal 59. In the preferred embodiment, both of the photodiode detectors 44 are connected in a balanced configuration so that the detector signals they produce have opposite amplitudes and tend to cancel when combined to produce the detector output signals 59. The balanced configuration provides some degree of additional sensitivity to moisture and improved dynamic range. The balanced configuration also tends to cancel the effects of the ambient light common in both emitter signals 42, thereby providing some immunity to ambient light. However, the detector output signal 59 still includes some unwanted signal components created by ambient light and electromagnetic interference.

Figure 3:
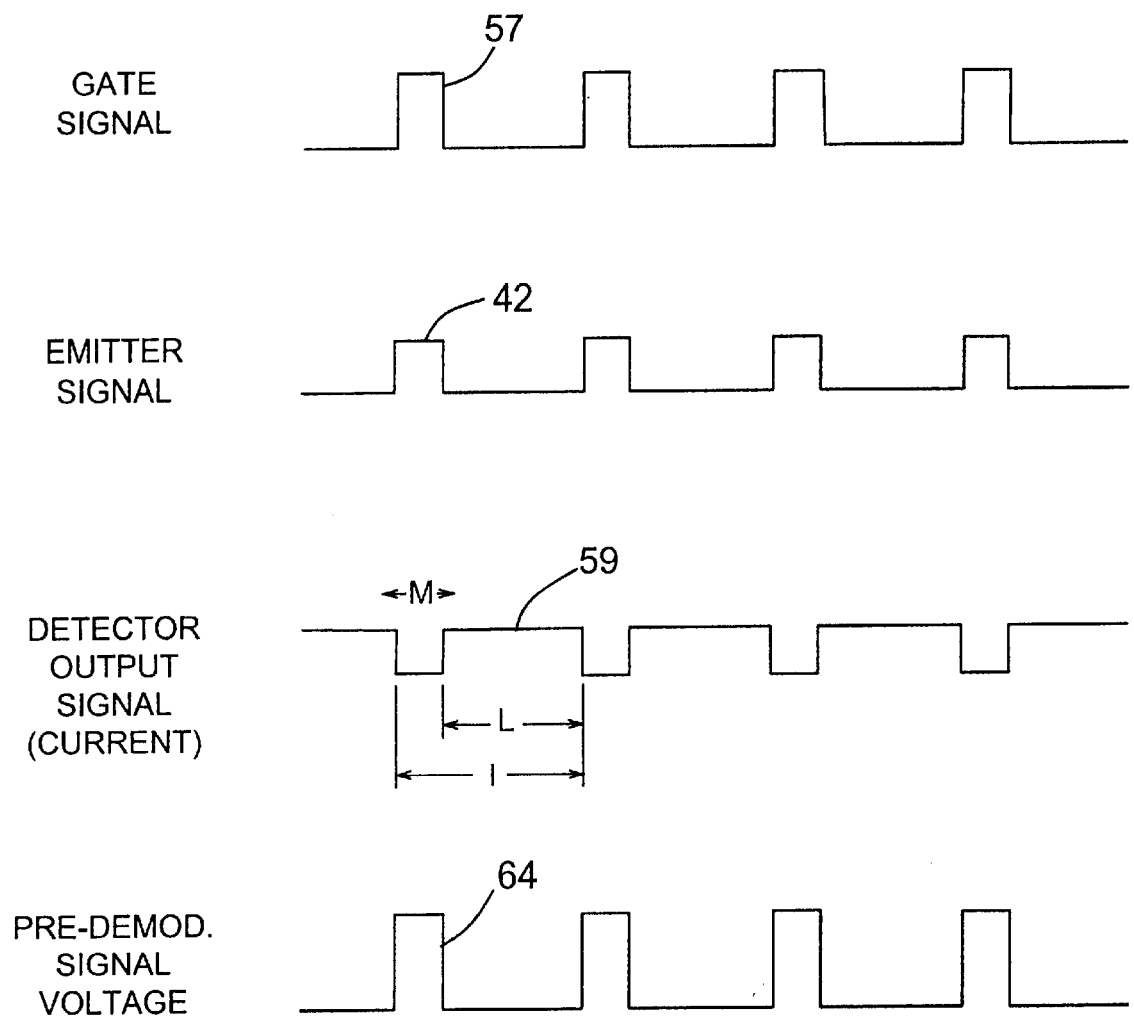
FIG. 3 is a graph illustrating the moisture sensor signals for the moisture sensor illustrated in FIG. 2.

Referring now to FIG. 3, the periodically repeating pulsed gate signal 57 received by the emitter driver 56 is illustrated.

The gate signal pulses 57 preferably have a 50-microsecond duration, and are repeated at a frequency of 1200 Hz, although any suitable duration and frequency may used. The emitter driver 56 is preferably a current source which responds to each gate signal pulse 57 by providing a pulse of current to the emitters 40. The emitters 40 respond to each current pulse by producing pulsed emitter signals shown at 42.

The detectors 44 allow current to flow in an amount proportional to the strength of the reflected emitter signals 42 they receive. The detector currents (not shown) are combined at node 58 to produce the detector output signal shown at 59. In the preferred embodiment, the detector output signal 59 is a pulsed current signal comprising a plurality of repeating signal intervals I. Each signal interval I has a duration of approximately 833 microseconds based on the gate signal pulse frequency of 1200 Hz described above, although any suitable duration may be used. Each signal interval I comprises a moisture sensing signal portion M which includes signal information about the reflected emitter signals 42 received by the detectors 44 as well as the effects of ambient light striking the detectors. Each signal interval I also has a light signal portion L when the emitters are not operated which includes the effects of the ambient light. The duration of each moisture sensing signal portion M is preferably 50 microseconds corresponding to the duration of the gate signal pulses 57.

Referring again to FIG. 2, the detector output signal 59 is coupled to the input 60a of a high gain, wide bandwidth pre-demodulation amplifier and filter circuit 60 to remove the undesirable signal components. The pre-demodulation amplifier and filter circuit 60 includes high pass filtering 61 for reducing effects of the ambient light disturbances by rejecting low frequency signal components of the detector output signal 59. The high pass filter 61 is preferably a fifth order filter having a corner frequency of 160 HZ for sharply attenuating the low frequency disturbances while passing most of the moisture sensing portion M of the detector output signal 59. However, any suitable order high pass filter having any suitable corner frequency may be used.

The pre-demodulation amplifier and filter circuit 60 also includes low pass filtering 62 for rejecting high frequency noise such as electromagnetic interference and random recombination of electrons and holes in the photodiodes 44. The low pass filter 62 is preferably a second order filter having a corner frequency of 33 KHZ for attenuating the high frequency disturbances while passing most of the energy present in the detector output signal 59. However, any suitable order low pass filter having any suitable corner frequency may be used. The preferred embodiment of the pre-demodulation gain and filtering circuit 60 uses multi-stage filters including two bandpass filters and three high pass filters (not shown) to achieve the fifth order high pass filter 61 and second order low pass filter 62. However, any suitable combination of filters may be used. Operational amplifiers, resistors and capacitors (not shown) are configured in a known manner to form the filters 61, 62.

The pre-demodulation amplification and filter circuit 60 also includes a gain stage 63 for amplifying the detector output signal 59. The amplifier 63 is preferably a transimpedance amplifier incorporated into one of the bandpass filters in a known manner, although any known signal amplifier may be used.

The pre-demodulation circuit 60 converts the pulsatile detector output current signal 59 into a filtered, amplified pulsatile pre-demodulation voltage signal 64 as shown in FIG. 3. The pre-demodulation signal 64 is sent from the pre-demodulation circuit output 60b to a microprocessor 65. The microprocessor 65 is preferably an 8-pin device, number PIC12C672 manufactured by Microchip Corporation, although any suitable microprocessor may be used.

The microprocessor 65 includes an analog to digital converter 66 which converts the analog pre-demodulation voltage pulses 64 to digital form for further processing by the microprocessor 65. The analog to digital converter 66 is preferably an 8-bit converter having a resolution a approximately 20 mV, although any suitable analog to digital converter having any suitable resolution may be used.

The digital signal is then demodulated in a demodulation stage 68 which demodulates the pulsatile signal to form a dc voltage signal 69 having an amplitude which represents the moisture detected by the sensor. Software within the microprocessor samples the sensed signal twice in rapid succession, once during the moisture sensing portion M of the signal interval I when the moisture sensing signal and the concomitant ambient light disturbances are present, and once during the light signal portion L of the signal interval I when just the ambient light signal is present. The effects of the ambient light disturbances are linearly subtracted through the software realization of a time-shifted linear differential amplifier, as taught by Teder in U.S. Pat. No. 5,059,877 which is incorporated herein by reference.

The output of the demodulation stage 68 is connected to a Digital Signal Processing (DSP) stage 70, in which software rejects both low and high frequency components of the noise induced by the high-gain pre-demodulation amplifier to a manageable level. The output of the DSP stage 70 thus has all noise effects dramatically attenuated, and responds almost exclusively to ambient light. The output of the DSP stage 70 is connected to a moisture event detection stage 72 which uses event detection software, preferably taught by Teder in U.S. Pat. No. 5,568,027. to produce an output signal 74 that indicates the presence of moisture on the glass surface.

The moisture event detection output 74 is connected to a moisture removal controller 76, which is preferably a vehicle wiper control unit. The vehicle wiper control unit includes a microprocessor capable of using the moisture event detection signals 74 to control the windshield wipers in response to moisture present on the glass.

The analog to digital converter 66 in the microprocessor 65 preferably has a resolution of approximately 20 mV. The resolution of the analog-to-digital converter 66 determines the smallest amount of change in the pre-demodulation signal 64 that can be detected. A/D converters having a higher resolution are typically more costly. Therefore, the pre-demodulation circuit uses the gain stage 63 for amplifying the detector output signal 59 so that small changes in this signal will be increased allowing the use of less expensive analog to digital converters having less resolution.

However, the high gain of the pre-demodulation circuit 60 can create undesirable results if the detector output signal 59 changes too much. The output of the gain stage 63 may only swing within a range set by the upper and lower limits of the sensor power supply (not shown). If the detector output signal 59 should cause the output of the gain stage 63 to reach either of those limits, the output can go no further and clipping occurs. Under these conditions, the amplifier 63 is saturated, no longer operating in the linear region where the output signal represents the input signal. It is desirable that saturation of the pre-demodulation amplifier be avoided so that the pre-demodulation signal accurately represents the detector output signal to provide correct operation of the moisture sensor.

Saturation can occur when one of the detectors 44 produces a much larger detector signal than the other detector resulting in a signal imbalance. The detector signals will not cancel each other as expected in the balanced configuration described above, and the detector output signal 59 will increase. Such an imbalance can occur by mounting the sensor 10 on a windshield such that one of the sensing regions 23 is in the shade band region of the windshield, or with the presence of a large amount of moisture over one of the sensing regions. A signal imbalance may also occur if an electronic component operates outside of its expected specifications. It would be undesirable for the moisture sensor 10 to lose accuracy under any of these conditions.

To prevent the signal imbalance from causing saturation of the pre-demodulation gain and filter circuit 60, the invention employs an auto-balance circuit 80, as shown FIG. 2. The autobalance circuit 80 includes a first switching element 82. The switching element 82 is preferably a gated solid state switch, such as the industry-standard type CD4066 which is known in the art, although any known switching element may be used. The switching element 82 includes an input 82a connected to the pre-demodulation gain and filter circuit output 60b, and an output 82b. The switching element 82 also includes a gate 82c for receiving a gate signal 57. When the gate signal reaches a predetermined level, the switch 82 closes and electrically connects the input 82a with the output 82b.

The switch output 82b is connected to an averaging circuit 86. The averaging circuit 86 is preferably a low pass filter, although any known circuit for providing an average of an input signal may be used. The low pass filter 86 preferably includes a resistor 88 connected to the first switching element output 82b and a capacitor 90 connected between the resistor 88 and ground. An operational amplifier (not shown) is preferably used to implement the low pass filter 86 in a known manner.

A second switching element 92 having an input 92a is connected to the output of the low pass filter 86. The second switching element 92 is similar to the first switching element 82, and includes an input 92a, an output 92b and a gate 92c. A gate signal 57 is provided to the gate 92c for closing the switch 92. A second resistor 96 is connected to the switch output 92b. The output of the autobalance circuit 80b provides an autobalance signal 98 to the input of the pre-demodulation circuit 60 as described below.

Figure 4:
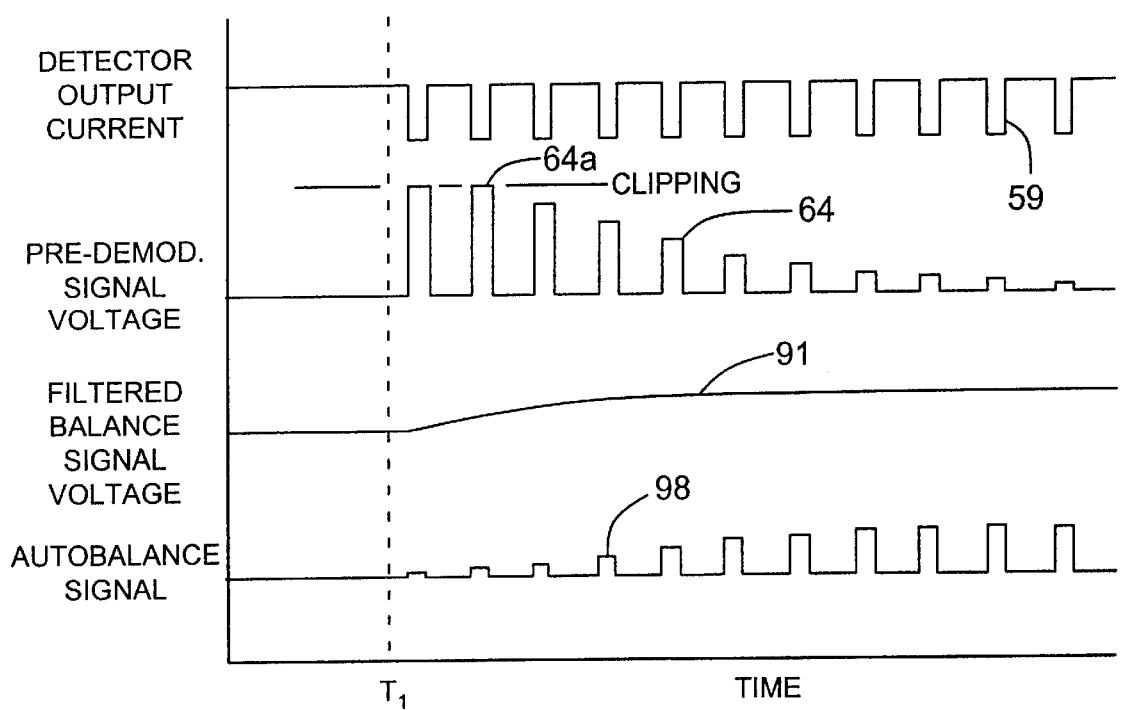
FIG. 4 is a graph illustrating moisture sensor signals and autobalance circuit signals in accordance with the invention.

Referring now to FIGS. 2 and 4, the operation of the autobalance circuit 80 shall now be described. At a time $T_1$, the photodetectors 44 become imbalanced as described above, resulting in the production of a high amplitude detector output current signal shown at 59. The high amplitude detector output signal 59 causes the pre-demodulation gain stage 63 to saturate thereby clipping the pre-demodulation signal 64 as shown at 64a in FIG. 4. The gate signal 57 causes the first switch 82 to close during the moisture portion M of each signal interval I allowing the clipped pre-demodulation signal 64 to be applied to the low pass filter 86. The capacitor 90 of the low pass filter 86 begins to charge and the low pass filter signal voltage 91 begins to rise as the average of the pre-demodulation signal 64 increases.

The second switch 92 is also closed by the gate signal 57, and the low pass filter signal 91 appears at the switch output 92b as a pulsatile voltage signal (not shown). The resistor 96 converts the pulsatile voltage to the pulsatile autobalance current signal 98. The autobalance signal 98 begins to increase in amplitude as the averaged signal voltage 91 increases. The autobalance signal 98 is connected to the pre-demodulation circuit input 60a. Since the overall gain of the pre-demodulation circuit is inverting, the autobalance signal current pulses 98 are in opposition to the detector output signal current pulses 59 and at least partially cancel the detector output signal current pulses. With the cancellation, the pre-demodulation signal 64 begins to decrease, and the amplifier 63 is brought back into the linear region of operation. Towards the end of the graph, the output pulses reach a steady-state amplitude that is much lower than it would be were it not for the effects of the autobalance circuit. The resistor 96 has a predetermined value which is used to determine the magnitude of the autobalance current pulses 98.

It can be seen that the autobalance circuit tends to cancel the effects of actual moisture events. The low pass filter 86 of the autobalance circuit, however, responds slowly, so that enough pulses get through the pre-demodulation circuit to the microprocessor to be detected before they are diminished in amplitude. The autobalance circuit operates in a similar fashion in canceling steady-state imbalances.

By partially canceling the detector signal, the autobalance circuit prevents the pre-demodulation gain stage from saturating. Because of this feature, the gain of the pre-demodulation circuitry may be made quite high. Therefore, even minuscule droplets will cause a large excursion in the output of the pre-demodulation circuitry. These excursions are readily detected by subsequent processing.

Also as a result of the autobalance circuitry, large drops do not cause the pre-demodulation circuitry to saturate. If a large drop should drive the output of the pre-demodulation circuitry into clipping, the autobalance circuit will quickly produce the appropriate signal to partially cancel the detector output signal. This will bring the pre-demodulation circuit output out of clipping and restore the sensor's ability to continue to detect moisture. Because all circuits are involved are linear, the sensor will be able to detect the addition of a small droplet of water, even in the presence of a large steady-state signal.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A method of detecting moisture on the surface of a material comprising:

providing a sensor mounted to the material and having an emitter for generating an emitter signal which is influenced by the presence of moisture on the surface of the material, and a detector for receiving the emitter signal and contributing to the production of a detector output signal;

filtering unwanted signal components from the detector output signal;

amplifying the detector output signal to produce an amplified signal; and at least partially canceling the detector output signal thereby reducing clipping of the amplified signal.

2. The method of detecting moisture defined in claim 1 wherein the amplified signal is inverted with respect to the detector output signal and the at least partially canceling step further includes combining the amplified signal with the detector output signal to at least partially cancel the detector output signal.

3. The method of detecting moisture defined in claim 2 further including averaging the amplified signal thereby producing an autobalance signal.

4. The method of detecting moisture defined in claim 3 wherein the averaging is provided by a low pass filter.

5. The method of detecting moisture defined in claim 4 further including providing a first switch for passing the amplified signal to the low pass filter.

6. The method of detecting moisture defined in claim 5 wherein the detector output signal includes a moisture sensing portion and further including passing the amplified signal with the first switch to the low pass filter during the moisture sensing portion.

7. The method of detecting moisture defined in claim 6 further including providing a second switch for passing the autobalance signal for combination with the detector output signal.

8. The method of detecting moisture defined in claim 7 further including passing the autobalance signal for combination with the detector output signal during the moisture sensing portion of the detector output signal.

9. A method of detecting moisture on the surface of a material comprising:
   providing a sensor mounted to the material and having an emitter for generating an emitter signal which is influenced by the presence of moisture on the surface of a material, and a detector for receiving the emitter signal and contributing to the production of a detector output signal;
   filtering and amplifying the detector output signal to produce a pre-demodulation signal;
   averaging the pre-demodulation signal to produce an autobalance signal;
   combining the autobalance signal with the detector output signal to at least partially cancel the detector output signal to prevent saturation of the pre-demodulation signal.

10. The method of detecting moisture defined in claim 9 wherein the autobalance signal is inverted with respect to the detector output signal.

11. The method of detecting moisture defined in claim 10 wherein the averaging step further includes providing a low pass filter for averaging the pre-demodulation signal.

12. The method of detecting moisture defined in claim 11 wherein the emitter signal and the detector output signal are pulsatile signals, and the detector output signal includes a regularly repeating signal interval having a moisture sensing signal portion.

13. The method of detecting moisture defined in claim 12 further including a first switch for passing the pre-demodulation signal during the moisture sensing signal portion of the detector output signal.

14. The method of detecting moisture defined in claim 13 further including providing a second switch for passing the autobalance signal during the moisture sensing signal portion of the detector output signal for combination with the detector output signal.

15. A method of detecting moisture on the surface of a material comprising:
   providing a sensor mounted to the material and having an emitter for generating an emitter signal which is influenced by the presence of moisture on the surface of the material, and a detector for receiving the emitter signal and contributing to the production of a detector output signal;
   filtering unwanted signal components from the detector output signal;
   amplifying the detector output signal to produce an amplified signal;
   generating an autobalance signal providing a delayed representation of the detector output signal; and
   combining the autobalance signal with the detector output signal to at least partially cancel the detector output signal thereby reducing clipping of the amplified signal.

16. The method of detecting moisture defined in claim 15 wherein the autobalance signal is an average of the detector output signal.

17. The method of detecting moisture defined in claim 15 wherein the autobalance signal is inverted with respect to the detector output signal.

18. A method of detecting moisture on the surface of a material comprising:
   providing a sensor for producing an output signal which is influence by the presence of moisture on the surface of the material;
   filtering unwanted signal components from the output signal;
   amplifying the output signal to produce an amplified signal;
   generating an autobalance signal providing a delayed representation of the output signal; and
   combining the autobalance signal with the output signal to at least partially cancel the output signal thereby reducing clipping of the amplified signal.

19. The method of detecting moisture defined in claim 18 wherein the autobalance signal is an average of the output signal.

20. The method of detecting moisture defined in claim 18 wherein the autobalance signal is inverted with respect to the output signal.

* * * * *